(12) United States Patent
Che et al.

(10) Patent No.: US 11,094,411 B2
(45) Date of Patent: Aug. 17, 2021

(54) METHODS AND DEVICES FOR PATHOLOGICALLY LABELING MEDICAL IMAGES, METHODS AND DEVICES FOR ISSUING REPORTS BASED ON MEDICAL IMAGES, AND COMPUTER-READABLE STORAGE MEDIA

(71) Applicant: GUANGZHOU KINGMED CENTER FOR CLINICAL LABORATORY CO., LTD., Guangdong (CN)

(72) Inventors: Shuanlong Che, Guangdong (CN); Pifu Luo, Guangdong (CN); Dong Liu, Guangdong (CN); Si Liu, Guangdong (CN); Hehua Liang, Guangdong (CN); Yinghua Li, Guangdong (CN); Weisong Qiu, Guangdong (CN); Juming Su, Guangdong (CN)

(73) Assignee: GUANGZHOU KINGMED CENTER FOR CLINICAL LABORATORY CO., LTD., Guangzhou (CN)

( * ) Notice: Subject to any disclaimer, the term of this patent is extended or adjusted under 35 U.S.C. 154(b) by 0 days.

(21) Appl. No.: 16/628,683

(22) PCT Filed: Jan. 28, 2019

(86) PCT No.: PCT/CN2019/073339
§ 371 (c)(1),
(2) Date: Jan. 6, 2020

(87) PCT Pub. No.: WO2020/082638
PCT Pub. Date: Apr. 30, 2020

(65) Prior Publication Data
US 2021/0035677 A1    Feb. 4, 2021

(30) Foreign Application Priority Data

Oct. 26, 2018  (CN) .......................... 201811260183.5
Oct. 26, 2018  (CN) .......................... 201811260195.8
(Continued)

(51) Int. Cl.
*G06K 9/00*   (2006.01)
*G16H 30/40*  (2018.01)
(Continued)

(52) U.S. Cl.
CPC ............... *G16H 30/40* (2018.01); *G06N 3/08* (2013.01); *G16H 30/20* (2018.01)

(58) Field of Classification Search
CPC .......... G06N 3/08; G16H 30/20; G16H 30/40; G06F 19/00; G06F 18/588; G06F 17/241; G06F 19/321
See application file for complete search history.

(56) References Cited

U.S. PATENT DOCUMENTS

2019/0172581 A1* 6/2019 Zlotnick ................ G06N 20/00

FOREIGN PATENT DOCUMENTS

CN    103926687 A    7/2014
CN    105975980 A    9/2016
(Continued)

OTHER PUBLICATIONS

Minghao Shen, Sensory Evaluation for Food, Jan. 31, 2017, p. 53, Zhengzhou University Press.

*Primary Examiner* — Xin Jia (57) ABSTRACT

Disclosed herein are a method and a device for pathologically labeling medical images, which is capable of effectively solving the problem associated with limitations on working location of artificial labeling, enhancing labeling
(Continued)

efficiency, and providing a huge number of learning samples with high quality with artificial intelligence.

16 Claims, 4 Drawing Sheets

(30) Foreign Application Priority Data

Oct. 26, 2018 (CN) .......................... 201811260198.1
Oct. 26, 2018 (CN) .......................... 201811261521.7

(51) Int. Cl.
*G16H 30/20* (2018.01)
*G06N 3/08* (2006.01)

(56) References Cited

FOREIGN PATENT DOCUMENTS

| | | | | |
|---|---|---|---|---|
| CN | 106845090 A | 6/2017 | | |
| CN | WO 2017101142 A1 * | 6/2017 | ............. | G06F 19/00 |
| CN | 107516005 A | 12/2017 | | |
| CN | 108510495 A | 9/2018 | | |
| WO | 2017101142 A1 | 6/2017 | | |

* cited by examiner

Figure 5 when receiving a request to perform labeling inputted by any one user, displaying a test interface and then randomly calling a medical images for testing user, obtaining labeling results for respective medical images from the user, wherein each of a medical images used for test has a correct labeling result, and wherein $a \geq 5$ — S1 comparing the labeling results for respective medical images from the user with the correct labeling results and obtaining the correct labeling rate for the a medical images made by the user — S2 determining that the user has qualification to perform labeling when judging that the correct labeling rate is higher than the preset first threshold — S3

Figure 6

S1 — obtaining an AI interpretation result for the medical image when receiving an instruction to issue a report for the medical image; wherein the AI interpretation result for the medical image comprises negative and positive results, and wherein, the AI interpretation result is obtained after interpretation by a preset classifier, which is trained by the reference labeling results for the medical images S2 — when the AI interpretation for the medical image is negative, sending a request for artificial interpretation result for the medical image to any one physician user S3 — when judging that the AI interpretation results for the medical images are negative, and the artificial interpretation results for the said medical images from the physician users are consistent with the said AI interpretation results, issuing a report for the medical images in which a negative result is indicated S4 — when judging that the AI interpretation results for the medical images are positive, sending a request for artificial interpretation results for the said medical images to any two physicians S5 — when judging that the AI interpretation results for the medical images are positive, and that both artificial interpretation results for the medical images from two physicians are consistent with the AI interpretation results, issuing a report for the medical images in which a positive result is indicated

Figure 7 device for pathologically labeling the medical image obtaining module 801 for pathological labeling qualification displaying module 802 for medical images saving module 803 for the first labeling result

METHODS AND DEVICES FOR PATHOLOGICALLY LABELING MEDICAL IMAGES, METHODS AND DEVICES FOR ISSUING REPORTS BASED ON MEDICAL IMAGES, AND COMPUTER-READABLE STORAGE MEDIA

CROSS REFERENCE TO RELATED APPLICATIONS

This application claims the benefits of, and priorities to, Chinese Invention Patent Applications Serial No. 2018112601958 with the title "METHODS AND DEVICES FOR PATHOLOGICALLY LABELING FOV IMAGES USED ON MOBILE TERMINAL", Serial No. 2018112601835 with the title "METHODS AND DEVICES FOR DETERMINING QUALIFICATION FOR PATHOLOGICALLY LABELING MEDICAL IMAGES", Serial No. 2018112601981 with the title "METHODS AND DEVICES FOR PATHOLOGICALLY LABELING MEDICAL IMAGES, AND COMPUTER-READABLE STORAGE MEDIUM", Serial No. 2018112615217 with the title "METHODS AND DEVICES FOR ISSUING REPORTS BASED ON MEDICAL IMAGES, AND COMPUTER-READABLE STORAGE MEDIA", filed on Oct. 26, 2018, the entire disclosures of which are hereby incorporated by reference.

FIELD OF THE INVENTION

The present invention relates to smart healthcare, more particular, to a method and a device for pathologically labeling medical images, and a method and a device for issuing reports based on medical images.

BACKGROUND OF THE INVENTION

Before machine learning is used for analysis of medical images, a huge number of labeling data with high quality are needed. Problems encountering and to be solved when applying artificial intelligence to clinical practice include how to ensure reliability of labeling quality and results and how to issue medical report by physicians under the help of artificial intelligence. There is no systemic method for demonstration and debugging accuracy of artificial intelligence. In order to apply artificial intelligence assistance diagnosis system from scientific research to clinical practice and to ensure accuracy and reliability of such system, good working procedure between physicians and artificial intelligence is required. It needs to have a mechanism to consistently study and make adjustment when problems that exist or will occur in artificial intelligence in future are found.

When artificial intelligence makes early labeling, it typically selects whole and integral labeling and middle FOV image labeling. Therefore, such artificial intelligence labeling can merely perform on large capacity computer with limitations on working locations. Labeling of a huge number of medical images cannot be achieved and thus learning samples cannot be supplied to artificial intelligence.

SUMMARY OF THE INVENTION

Generally, the present disclosure provides a method and a device for pathologically labeling medical images, a computer-readable storage medium, which is capable of effectively solving the problem associated with limitations on working location of artificial labeling, enhancing labeling efficiency, and providing a huge number of learning samples with high quality with artificial intelligence.

In one embodiment, provided herein is a method for pathologically labeling medical images, comprising:

judging whether a user has qualification for performing pathological labeling when receiving a request for entering into the labeling mode, which is inputted by the user on a mobile terminal;

randomly calling medical images to be labeled and displaying the same at a display interface of the mobile terminal when judging that the user has qualification for performing pathological labeling;

receiving and saving a first labeling result for the medical images from the user;

wherein:

the medical images are generated by the following steps:

dividing the original scanning image of the pathological section into n FOV images and then calculating pathological index of each FOV image, wherein, $10^{\wedge}10 \geq n \geq 10$; and the storage space occupied by FOV images is less than the preset threshold;

obtaining the first m FOV images with the highest pathological index among n FOV images, wherein, $50 \geq m \geq 5$.

As compared with the prior arts, the method for pathologically labeling medical images as described herein comprises: judging whether a user has qualification for performing pathological labeling when receiving a request for entering into the labeling mode, which is inputted by the user on a mobile terminal; randomly calling medical images to be labeled and displaying the same on a display interface of the mobile terminal when judging that the user has qualification for performing pathological labeling; receiving and saving a first labeling result for the medical images from the user. The medical images are generated by the following steps: dividing the original scanning image of the pathological section into n FOV images and then calculating pathological index of each FOV image, wherein, $10^{\wedge}10 \geq n \geq 10$; and the storage space occupied by FOV images is less than the preset threshold; obtaining the first m FOV images with the highest pathological index among n FOV images, wherein, $50 \geq m \geq 5$. The operator for labeling does not need to perform whole and integral labeling, and just performs labeling on small images obtained by division. Therefore, the workload of the operator for labeling will be reduced with decreased fatigue, and increased labeling accuracy. And the labeling can be performed on a mobile terminal anytime at anywhere without limitations on location in favor of enhancing working efficiency so as to provide a huge number of learning samples with high quality with artificial intelligence.

As an improvement on the above solution, the method as described herein further comprises the following steps:

judging whether two first labeling results from two users are consistent with each other when detecting that any medical image has two first labeling results from two users;

when the two first labeling results from two users are consistent with each other, using the two first labeling results as reference labeling results of the medical image, and increasing the numbers of correction labeling for these two users by 1.

As an improvement on the above solution, the method as described herein further comprises the following steps:

randomly sending a request for labeling medical image to any other users or expert users, when judging that the two first labeling results from two users are inconsistent with each other.

As an improvement on the above solution, the method as described herein further comprises the following steps:

randomly sending a request for labeling medical image to any other users or expert users, when judging that the two first labeling results from two users are inconsistent with each other;

when receiving a second labeling result from other users or expert users, using the said second labeling result as a reference labeling result for the medical image, and increasing the incorrect labeling numbers for the user whose first labeling result is inconsistent with the second labeling result by 1, and increasing the correct labeling numbers for the user whose first labeling result is consistent with the second labeling result by 1.

As an improvement on the above solution, the method as described herein further comprises the following steps:

cancelling the user's qualification for pathologically labeling when detecting that the numbers of the incorrect labeling of any one user are higher than preset first threshold.

As an improvement on the above solution, the method as described herein further comprises the following steps:

adding the medical image to the difficult case library when receiving a request for adding the medical image to the difficult case library from other user or expert user.

As an improvement on the above solution, the method as described herein further comprises the following steps:

obtaining AI labeling result of the medical image when displaying the medical image, wherein the AI labeling result of the medical image includes positive and negative results;

when the AI labeling result of the medical image is negative and the first labeling result of the medical image from any one user is consistent with the AI labeling result of the medical image, using the AI labeling result of the medical image as a reference labeling result of the medical image;

when the AI labeling result of the medical image is positive and neither of the first labeling results of the medical image from any two users are consistent with the AI labeling result of the medical image, using the first labeling results of the medical image from the two users as a reference labeling result of the medical image;

when the AI labeling result of the medical image is positive and the first labeling result of the medical image from one user of any two users is inconsistent with the AI labeling result of the medical image, randomly sending a request for labeling the medical image or for organizing discussion to any one other user or expert user;

when receiving the second labeling result from other user or expert user, using the second labeling result from other user or expert user as a reference label result of the medical image;

when receiving the third labeling result generated after discussion of any two users and other user or expert user, using the third labeling result as a reference labeling result of the medical image.

As an improvement on the above solution, the judging whether a use has qualification for performing pathological labeling comprises:

when receiving a request for label qualification from the user, displaying a test interface and randomly calling a numbers of medical images for testing the user, then obtaining the labeling results for respective medical images, wherein all of a numbers of medical images for testing the user have correct labeling result, and a≥5;

comparing the labeling result for each medical image from user with the correct labeling result and obtaining correct labeling rate for a numbers of medical images with correct labeling results;

determining that the user has labeling qualification when the correct labeling rate is higher than the preset second threshold.

As an improvement on the above solution, the judging whether a use has qualification for performing pathological labeling further comprises:

when judging that the correct labeling rate is lower than the preset second threshold, judging whether the correct labeling rate is higher than preset third threshold;

when judging that the correct labeling rate is higher than the preset third threshold, if receiving a training request from the user, displaying the training interface and calling x numbers of medical images for training the user, wherein all of x numbers of medical images for training the user have correct labeling result, wherein x≥5.

As an improvement on the above solution, the judging whether a use has qualification for performing pathological labeling further comprises:

when judging that the correct labeling rate is lower than the preset third threshold, displaying a learning interface, on which systemic knowledge for labeling is displayed.

As an improvement on the above solution, the judging whether a use has qualification for performing pathological labeling further comprises:

when judging that the correct labeling rate is lower than the preset third threshold, refusing the training request and the request for labeling qualification from the user within preset period;

when judging that the correct labeling rate is lower than the preset third threshold, re-receiving the training request and the request for labeling qualification from the after the preset period.

As an improvement on the above solution, the receiving and saving the first labeling result from the user comprises:

displaying first option buttons for selecting whether there are lesion cells and what type of the lesion cells at the displaying interface, when displaying the medical images;

when receiving the clicking operation on any one of first option buttons from the user, obtaining and saving the first labeling result on the medical image from the user.

As an improvement on the above solution, the obtaining the first labeling result on the medical image from the user when receiving the clicking operation on any one of first option buttons from the user comprises:

when displaying the medical images, displaying the labeling results for the medical results from other users or machines at the displaying interface, and meanwhile displaying the second option buttons for selecting whether agreeing the labeling results for the medical images from other users or machines;

when receiving the clicking operation on any one of second option buttons from the user, obtaining the first labeling result for the medical image from the user.

As an improvement on the above solution, the second option buttons includes an agreement button and a disagreement button.

When receiving the clicking operation on any one of the first option buttons from the user, obtaining the first labeling result for the medical image from the user specifically includes:

when receiving the clicking operation on the agreement button from the user, using the labeling result of the medical image from other users or machines as the first labeling result from the user;

when receiving the clicking operation on the disagreement button from the user, using the labeling result that is re-input by the user as the first labeling result from the user.

As an improvement on the above solution, the method as described herein further comprises the following steps:

displaying a voice inputting mark at the time of displaying the second option buttons, wherein the displaying status of the voice inputting mark includes detection of the voice inputting status and termination of detection of the voice inputting status.

When receiving the clicking operation on disagreement button from the user, using the labeling resulting that is inputted by the user as the first labeling result from the user specifically includes:

when receiving the clicking operation on the disagreement button from the user, changing the displaying status of the voice inputting mark to detection of the voice inputting status and obtaining the labeling result that is inputted by the user by a voice device and using the same as the first labeling result.

As an improvement on the above solution, the voice inputting mark is a progress bar for voice inputting. When the displaying status of the voice inputting mark is shown as termination of detection of voice inputting status, the displaying interface shows that the progress bar for voice inputting is in full grid status. When the displaying status of the voice inputting mark is shown as detection of voice inputting status, the displaying interface shows that the progress bar for voice inputting is decreasing within preset period.

Provided herein is a method for issuing reports based on medical images, comprising the following steps:

obtaining an AI interpretation result for the medical images when receiving an instruction to issue a report associated with any one medical image, wherein the AI interpretation result for the medical images includes negative and positive results, wherein the AI interpretation result for the medical images is obtained after judging by a preset classifier that is trained by the reference labeling result for the medical image as described above;

when the AI interpretation result for the medical image is negative, sending a request for an artificial interpretation result for the medical image to any one physician;

when the AI interpretation result for the medical image is negative and the artificial interpretation result for the medical image from the physician is consistent with the AI interpretation result, issuing a report for the medical image in which the negative result is indicated.

when the AI interpretation result for the medical image is positive, sending a request for artificial interpretation result for the medical image to two physicians;

when the AI interpretation result for the medical image is positive and the artificial interpretation results for the medical image from the two physicians are consistent with the AI interpretation result, issuing a report associated with the medical image in which the positive result is indicated.

As an improvement on the above solution, the method as described herein further comprises the following steps:

when the AI interpretation result for the medical image is positive, and the artificial interpretation result for the medical image from at least one of the two physicians is inconsistent with the AI interpretation result, sending a request for making judgement or organizing discussion to other physicians or expert users.

As an improvement on the above solution, the method as described herein further comprises the following steps:

when receiving the artificial interpretation result for the medical image from other physicians or expert user, issuing a report associated with the medical image in which the artificial interpretation result for the medical image from other users or expert users is indicated.

As an improvement on the above solution, the method as described herein further comprises the following steps:

when receiving the final artificial interpretation result obtained by discussion with the two physicians and other users or expert users, issuing a report associated with the medical image in which the final interpretation result is indicated.

In another embodiment, provided herein is a device for pathologically labeling medical image, comprising a processor, a memory and a computer program that is stored in the memory and configured to be executed by the processor, wherein the method for pathologically labeling the medical image as described herein is achieved when the computer program is executed by the processor.

In another embodiment, provided herein is a computer-readable storage medium, comprising a computer program stored therein, wherein the computer-readable storage medium is controlled to execute the method for pathologically labeling the medical image as described herein on the device as described herein.

In another embodiment as described herein, provided herein is a device for pathologically labeling medical image, comprising a processor, a memory, and a computer program that is stored in the memory and configured to be executed by the processor, wherein the method for issuing the report based on the medical image as described herein is achieved when the computer program is executed by the processor.

In yet another embodiment as described herein, provided herein is a computer-readable storage medium, comprising a computer program stored therein, wherein the computer-readable storage medium is controlled to execute the method for issuing the report based on the medical image as described herein on the device herein when operating the computer program.

BRIEF DESCRIPTION OF THE DRAWINGS

FIG. 7 is a flow diagram illustrating a method for issuing a report based on the medical image according to one embodiment as described herein.

FIG. 8 is a structural diagram illustrating a device for pathologically labeling the medical image according to one embodiment as described herein.

DETAILED DESCRIPTION OF THE INVENTION

Several aspects of the invention are described below in details by reference to appended drawing and specific embodiments. The skilled in the art should understand that the embodiments are set forth to provide an illustration, rather than limit the scope of the present invention. The scope of the present invention is limited by the appended claims.

The terminology used herein is for the purpose of describing particular embodiments only and is not intended to be limiting of the invention. As used herein, the singular forms "a", "an" and "the" are intended to include the plural forms as well, unless the context clearly indicates otherwise.

Figure 1:
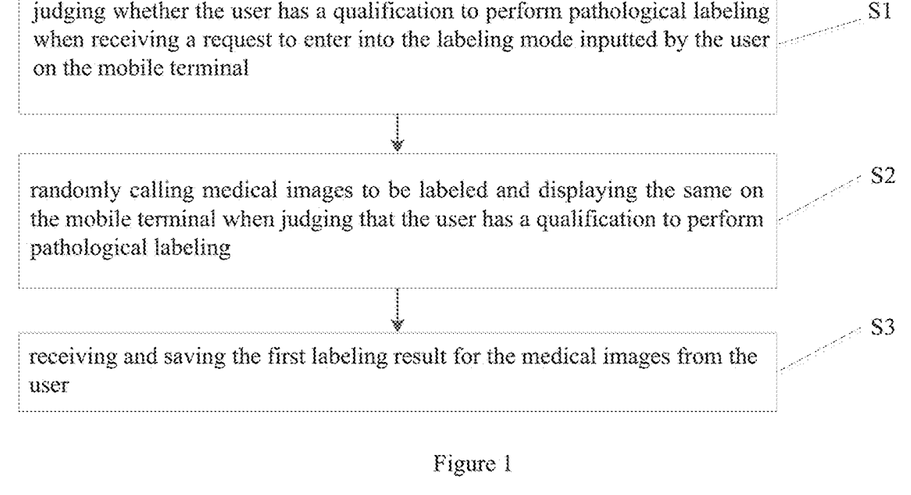
FIG. 1 is a flow diagram illustrating a method for pathologically labeling medical images according to one embodiment as described herein.

Referring to FIG. 1, it shows a flow diagram illustrating a method for pathologically labeling medical images according to one embodiment as described herein, which is used to one mobile terminal and comprises the following steps:

S1. judging whether a user has qualification to perform pathological labeling when receiving a request for entering into labeling mode inputted by any one user on the mobile terminal; wherein, the user is subject to specific test to receive qualification for pathological labeling, for example, s medical images are randomly called to perform test for the user, and then the labeling results for respective medical images from the user are obtained, the labeling results for respective medical images from the user are compared with the correct labeling results, and then the correct labeling rate for the medical images with correct labeling results for s medical images can be obtained; when the correct labeling rate is higher than the preset first threshold, the user is determined to have qualification to perform pathological labeling; high medical level, and consistency and stability as well as quality of labeling are ensured by using specific test to screen user for labeling, thereby obtaining objective and scientific evaluation index and facilitating construction of machine learning mode;

S2. randomly calling medical images to be labeled and displaying them on the displaying interface of the mobile terminal, when judging that the user has qualification to perform pathological labeling.

In the step S1, preferably, the medical image is generated by the following steps.

Figure 2:
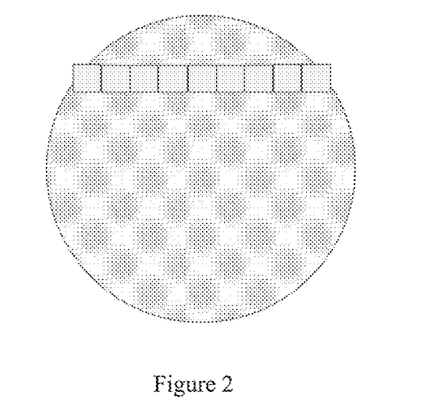
FIG. 2 is a divided diagram illustrating the original scanning image of the pathological section according to one embodiment as described herein.

As shown in FIG. 2, the original scanning image of the pathological section is divided into n FOV images and then the pathological index of each FOV image among n FOV images is calculated, wherein $10^{\wedge}10 \geq n \geq 10$, and the storage space occupied by the FOV images is less than the preset threshold.

Based on the pathological index of each FOV image among n images, the first m FOV images with the highest pathological index among n FOV images is obtained as the medical images, wherein $50 \geq m \geq 5$.

The above calculation of the pathological index for each FOV images among n images is carried out by artificial intelligence. For example, 20 images are screened from a huge number of images by using artificial intelligence and displayed in order, such that the working load for the physicians is significantly decreased.

Figures 3A, 3B:
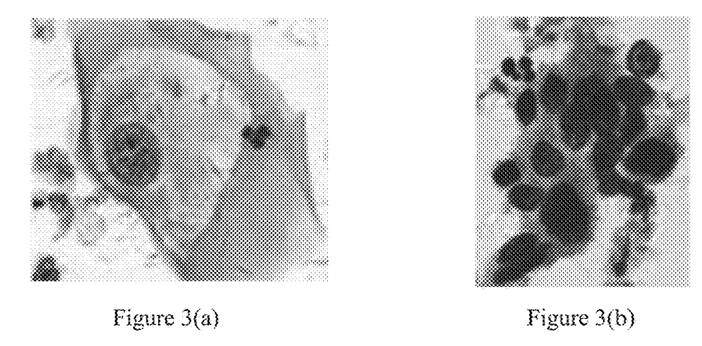
FIG. 3(a) is a single-cell small dividing picture of cervix cells.
FIG. 3(b) is a small dividing picture of cell mass of cervix cells.

In general, the original scanning images are obtained as ×400 digital images with size between server Gs and dozens of Gs by scanning and converting the cell pathological slides using cell pathology slides. If the labeling operator makes labeling on whole images, the working load will be very huge and such labeling only can be done on large capacity computer, thereby resulting in limitations on working locations. Therefore, there are problems such as missing labeling, complicated labeling steps and huge working load in the original labeling work. After dividing the original digital image, the labeling operator can perform labeling anywhere at any time, and there is no need for the large capacity computer to load divided images, thereby reducing the working load of the labeling operator. As shown in FIG. 3(a), it shows divided images of cervix single-cell. As shown in FIG. 3(b), it shows divided images of cervix cell mass.

In addition, the small images can be readily uploaded and downloaded to and from various receiving platform via internet, and can be readily transferred to mobile devices from the Cloud, thereby achieving rapid operation and completing labeling. Therefore, the labeling operators can perform test labeling using mobile terminals (such as, cell phone and the like) in free time (such as waiting for buses, or taking buses and the like). Also, the labeling operators can perform labeling using common PC at home or at office, using various devices via synchronous operation, thereby enhancing convenience and utilizing free time at the most extent.

S3. receiving and saving the first labeling result for the medical image from the user.

Figure 4:
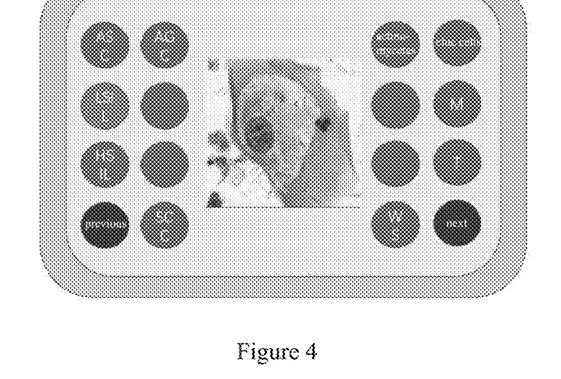
FIG. 4 is a diagram illustrating displaying interface of the mobile terminal according to one embodiment as described herein.

For example, as shown in FIG. 4, at the displaying interface of the mobile terminal, in addition to the medical image, it shows first option buttons surrounding the medical image for selecting whether there are malignant cells and what kind of the malignant cells (including ASC, LSIL, AGC, HSIL etc.) is. When receiving the selection operation on the first option buttons from the user, this operation is saved and the next medical image is automatically showed. In general, probability that the labeling result is LSIL is the highest. Therefore, the system has defaults that the user selects LSIL and the locations for various labeling options can be adjusted according to probability of lesion distribution, thereby enhancing friendliness and convenience of the operation system.

When displaying the medical images, the labeling results for the medical images made by other users or machines are also shown at the displaying interface and meanwhile, second option buttons for selecting whether agreeing the labeling results for the medical images made by other users or machines.

When receiving the clicking operation on the second option buttons from the user, the first labeling result for the medical image from the user is obtained.

The second option buttons include an agreement button and a disagreement button.

When receiving the clicking operation on the first option buttons from the user, the first labeling result for the medical image from the user is obtained by the following steps:

when receiving the clicking operation on the agreement button from the user, using the labeling results for the medical images made by other users or machines as the first labeling result of the user;

when receiving the clicking operation on the disagreement button from the user, using the labeling result re-inputted by the user as the first labeling result of the user.

Figure 5:
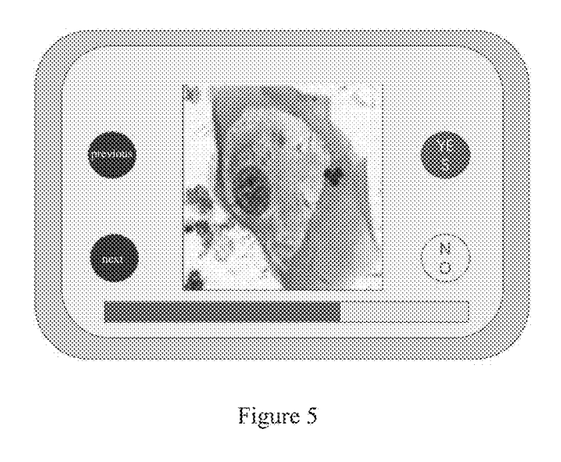
FIG. 5 is a diagram illustrating displaying interface of the mobile terminal according to another embodiment as described herein.

For example, as shown in FIG. 5, at the displaying interface of the mobile terminal, in addition to the medical images, it shows previous artificial labeling results or machine labeling results and meanwhile, it shows second option buttons for selecting whether agreeing the labeling results for the medical images made by other users or machines (i.e., button "YES" and button "NO" in FIG. 5). If correct, the user clicks the button "YES", the result of the clicking operation is saved and next medical image is showed. If incorrect, the user clicks the button "NO" and re-inputs new labeling result. Through such re-checking method, the wrong labeling results can be corrected rapidly and the complexity for operation is reduced utmostly.

From the displaying interface of FIGS. 4 and 5, it can be seen that the solution of the present invention also considers friendliness and gameplay of the labeling interface, thereby decreasing discomfort and fatigue for the physicians for pathological labeling.

When displaying the second option buttons, a voice inputting mark is also displayed at the same time, wherein, the displaying status of the voice inputting mark includes detection of voice inputting and termination of detection of voice inputting.

When receiving the clicking operation on the disagreement button from the user, the labeling result re-inputted by the user is served as the first labeling result of the user, including the followings:

When receiving the clicking operation on the disagreement button from the user, the displaying status of the voice inputting mark is changed to detection of voice inputting and the labeling result inputted by the user via the voice device is served as the first labeling result from the user.

Preferably, the voice inputting mark is a progress bar for voice inputting. When the displaying status of the voice inputting mark is termination of detection of voice inputting, the progress bar for voice inputting is shown as full grid at the displaying interface. When the displaying status of the voice inputting mark is detection of voice inputting, the progress bar for voice inputting is shown as gradual decrease at the displaying interface.

For example, as shown in FIG. 5, when the labeling operator clicks button "NO", error correction function within count-down 5 to 10 seconds is shown and the progress bar for voice inputting is shown as gradual decrease. For example, for a LSIL image, which is previously labeled as ASC-US, after the labeling operator says LSIL, the mobile terminal will do automatic error correction.

In one preferable example, when detecting that any one medical image has first labeling results from two users, it needs to judge whether the first labeling results from two users are consistent or not with each other.

When judging that the first labeling results from two users are consistent with each other, such first labeling results from two users are used as reference labeling results for the medical image and the correct labeling numbers for these two users are increased by 1.

When judging that the first labeling results from two users are inconsistent with each other, a request for labeling the medical image is randomly sent to any one user or expert user.

When receiving the second labeling result for the medical image from other user or expert use, such second labeling result is used as the reference labeling result for the medical image and the incorrect labeling numbers for the user whose first labeling result is inconsistent with the said second labeling result is increased by 1, and the correct labeling numbers for the user whose first labeling result is consistent with the said second labeling result is increased by 1.

Through the above solution, the same medical image is randomly allocated to two different labeling operators to evaluate and label the same case online, which leads to double check system, such that systematic error existing in the artificial intelligence due to design can be avoided and the reliability and accuracy of the labeling can be ensured.

In addition, when detecting that the incorrect labeling numbers of any one user is higher than the preset first threshold, the qualification for pathological labeling for this user is cancelled. Through monitoring and eliminating system, bugs due to random operation and lack of diagnosis capacity can be avoided. When detecting that the correct labeling numbers of any one user is higher than the preset second threshold, this user will be incorporated into expert labeling operator library. When detecting that the correct labeling numbers of any one user is higher than the preset third threshold and this user holds Certificate of Medical Practitioner, a qualification for issuing report will be granted to this user. In addition, users' rank according to the correct labeling numbers can be displayed at the displaying interface. As such, the labeling efficiency of the users can be enhanced so as to achieve labeling for a huge number of medical images.

Except for asking other users or expert users to perform labeling for medical images, organization of experts to discuss and reach an agreement can be performed. Furthermore, when receiving a request for incorporating the medical image into the difficult case library from other users or expert users, such medical image will be incorporated into difficult case library as atypical case for study.

In another example, the method of the present invention further comprises the following steps:

obtaining AI labeling results for the medical images when displaying the medical images, wherein the AI labeling results comprise positive and negative results;

when the AI labeling results for the medical images are negative and the first labeling result for the medical image from any one user is consistent with the AI labeling results, using the AI labeling results for the medical images as reference labeling results for the medical images;

when the AI labeling results for the medical images are positive and both of the first labeling results for the medical image from any two users are consistent with the AI labeling results, using the AI labeling results for the medical images as reference labeling results for the medical images;

when the AI labeling results for the medical images are positive and neither of the first labeling results for the medical image from any two users is consistent with the AI labeling results, using the first labeling results for the medical image from any two users as reference labeling results for the medical images;

when the AI labeling results for the medical images are positive and the first labeling result for the medical image from one of any two users is inconsistent with the AI labeling results, randomly sending a request for labeling the medical images or a request for organizing discussion to any one of other users or expert users;

when receiving the second labeling results for the medical images from other users or expert users, using the second labeling results for the medical images from other users or expert users as reference labeling results for the medical images;

when receiving the third labeling results for the medical images obtained after discussion between any two users and other users or expert users, using the third labeling results for the medical images as reference labeling results.

In sum, in virtue of the method as described herein, the labeling operators can perform labeling for the medical images anywhere at any time with maintaining labeling quality, without limitations on working locations, such that the efficiency of working mode is improved, the quality and efficiency of medical service is significantly increased, thereby providing artificial intelligence with a huge number of learning samples with high quality. Furthermore, for each user, he/she randomly obtains medical image, while for each medical image, it is randomly allocated to user. Objective interpretation of medical images can be achieved utmostly, thereby reducing diagnostic difference among various areas and hospitals, and ensuring patients to accept uniform healthcare.

Figure 6:
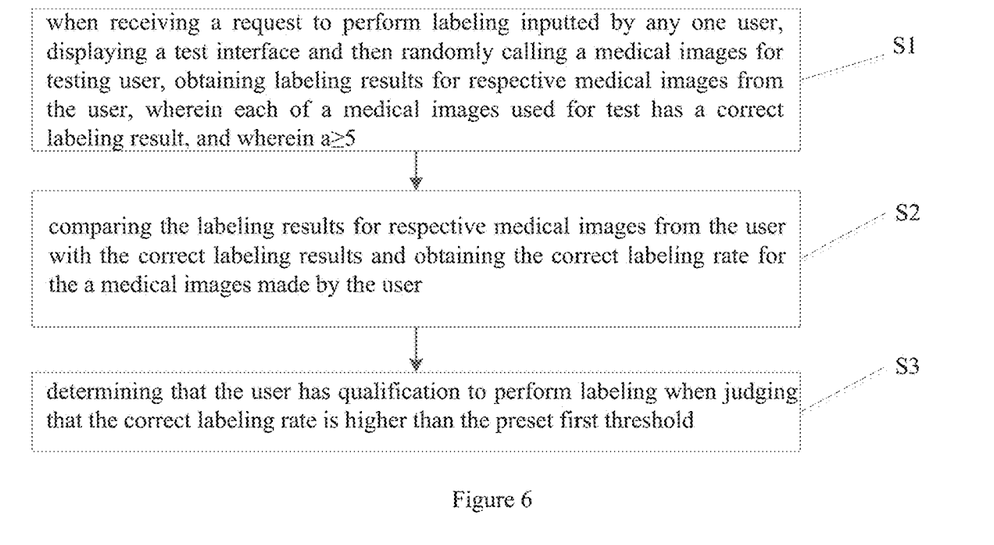
FIG. 6 is a flow diagram illustrating determination whether the user has qualification for pathological labeling according to one embodiment as described herein.

In one preferable example, as shown in FIG. 6, determination whether the user has qualification to perform pathological labeling comprises the following steps:

S11. when receiving a request for labeling qualification inputted by the user, displaying a test interface and randomly calling a medical images for performing test for the user, obtaining the labeling results for respective medical images from the user, wherein each of a medical images used for test has a correct labeling result, and wherein a≥5;

S12. comparing the labeling results for respective medical images made by the user with the correct labeling results and then obtaining the correct labeling rate for the medical images made by the user; in practical operation, the numbers (a) for test is not limited, when a is higher than a certain number, it can be understood that, in the case that the numbers for test is small, it is desirable to have increased correct labeling numbers; wherein, obtaining the correct labeling rate for the medical images comprising: dividing the numbers of the labeling results for the medical images made by the user, which are consistent with the correct labeling results, by the numbers (a), to obtain the correct labeling rate made by the user for the a medical images;

S13. when the correct labeling rate is higher than the preset second threshold, determining that the user has labeling qualification.

For example, when the correct labeling rate is higher than 0.95, it can be considered that the labeling physician has high medical level, with stable consistency, such that it can be determined that the user has a labeling qualification and can be a labeling operator to train machine learning.

Therefore, in the present example, the labeling operator is screened by consistent test, such that high medical level is maintained and labeling qualification is consistent and stable. In addition, in virtue of the solution of the present example, the labeling operator is screened based on labeling qualification rather than seniority, such that subjective deviation caused by using seniority physician as screening criterion for labeling operator can be avoided. For example, seniority labeling physician typically focuses on one specialized subclass, while he/she may be not good at other subclasses. Therefore, according to the solution of the present example, the labeling qualification can be ensured and objective evaluation can be achieved, thereby facilitating construction of machine learning mode in future.

In another preferable example, when judging that the correct labeling rate is lower than the preset second threshold, it needs to judge whether the correct labeling rate is higher than the preset third threshold or not.

When the correct labeling rate is higher than the preset third threshold, if receiving a training request from the user, a training interface is displayed, and x medical images for training the user are called, wherein, the x medical images for training the user have correct labeling results and wherein x≥5.

For example, in the case that the correct labeling rate for user test is lower than 0.95 but higher than 0.50, which may be rendered due to misoperation or lack of knowledge on specific lesion, the user can apply for learning test questions online firstly, and then apply for preliminary test for preliminarily screening again. In the case that the correct labeling rate is higher than 0.95, it can be determined that the user has labeling qualification. If the correct labeling rate is still lower than 0.95 and higher than 0.50, the user needs to enter into training mode to receive training, followed by re-sending a request for labeling qualification.

In addition, when judging that the correct labeling rate is lower than the preset third threshold, the request for training and labeling qualification from the user will be refused within a preset period, i.e., forbidding the user's account, and a learning interface will be displayed. At this learning interface, the systematic knowledge about labeling will be displayed for training the user with comprehensive knowledge. After the preset period, the request for training and labeling qualification from the user will be accepted again.

For example, when the correct labeling rate is lower than 0.50, it may be rendered due to insufficient diagnostic level and thus the user may have to receive a systematic learning on a specialized subclass. After forbidding the user's account for a certain period (e.g., 24-48 h), the user can apply for learning test questions and preliminary test for preliminarily screening online again.

As shown in FIG. 7, the present example further provides a method for issuing a report based on the medical image, comprising the following steps:

S71. obtaining an AI interpretation result for the medical image when producing an instruction to issue a report for the medical image; wherein the AI interpretation result for the medical image comprises negative and positive results, and wherein, the AI interpretation result is obtained after interpretation by a preset classifier, which is trained by the reference labeling results for the medical images as provided;

S72. when the AI interpretation for the medical image is a negative result, sending a request for artificial interpretation result for the medical image to any one physician user.

In particular, the physician is the user having qualification for issuing report, who typically holds Certificate of Medical Practitioner.

Since the medical image is a divided small image, which can be uploaded to the mobile terminal of the physician to display, the physician could perform labeling by using the mobile terminal (e.g., cell phone and the like) at free time (e.g., taking a bus, or waiting for a bus and the like). Alternatively, the physician could perform labeling at home or office by using common PC and the labeling can be performed synchronously by using different devices. As such, convenience for performing labeling is enhanced and the free time of the physician user can be utilized to perform labeling at the greatest extent. Furthermore, since the small images are screened by artificial intelligence, the working load of the physician is greatly decreased and the risk due to fatigue is reduced.

S73. when judging that the AI interpretation results for the medical images are negative, and the artificial interpretation results for the said medical images from the physician users are consistent with the said AI interpretation results, issuing a report for the medical images in which a negative result is indicated.

In step S73, since the probability of the negative results is much higher than that of positive results, error rate is low and the report can be issued without double-check by several physician users.

S74. when judging that the AI interpretation results for the medical images are positive, sending a request for artificial interpretation results for the said medical images to any two physicians.

In step S74, since the AI interpretation results are judged to be consistent with the artificial results from any two physician users, the objectivity of the positive results is ensured to avoid error due to deviation of interpretation results from only one physician user. Also, in the medical field, the probability of positive results is low. Therefore, it needs to do double-check from two physicians to issue a report.

S75. when judging that the AI interpretation results for the medical images are positive, and that both artificial interpretation results for the medical images from two physicians are consistent with the AI interpretation results, issuing a report for the medical images in which a positive result is indicated.

It can be understood that if both physicians agree with the AI interpretation results, it demonstrates that the AI interpretation results have high objectivity and accuracy and thus a report for the medical images can be issued.

For the mobile terminal of the physician user, when receiving a request to perform artificial interpretation, the medical images and AI interpretation results are displayed at the displaying interface, and meanwhile, a third option button indicating whether agreeing the AI interpretation results for the medical images is also displayed. The third option button comprises an agreement button and a disagreement button.

When receiving a clicking operation on the agreement button by the physician user, it can be determined that the artificial interpretation result from this physician user is consistent with the AI interpretation results for the medical images.

When receiving a clicking operation on the disagreement button by the physician user, it can be determined that the artificial interpretation result from this physician user is inconsistent with the AI interpretation results for the medical images.

In the present example, the artificial intelligence can be used for issuing report in clinical practice, which facilitates development of medical intellectualization, enhances efficiency of issuing reports, and ensures medical safe in aid of artificial intelligence. Therefore, the medical quality can be maintained in a high level even if the number of patient is increased.

In addition, based on the above example, another example further comprises the following steps:

when judging that the AI interpretation results for the medical images are positive, and that at least one of two physicians makes artificial interpretation results for the medical images which are inconsistent with AI interpretation results, sending a request for making interpretation results for the medical images or organizing a discussion to other physician users or expert users;

when receiving the artificial interpretation results for the medical images from other physician users or expert users, issuing a report about the medical images and indicating the artificial interpretation results of other users or expert users in the said report;

when receiving final artificial interpretation results made after discussion among two physician users and other physician users or expert users, issuing a report about the medical images and indicating the final artificial interpretation results in the said report.

It should note that, the labeling users as disclosed herein are different from the physician users. In particular, the labeling users have qualification to perform pathological labeling, while the physician users have qualification to issue report, to which they are responsible, in addition to pathological labeling. Users need to accept specific test to be granted qualification to perform pathological labeling. For example, a medical images (a≥10) can be randomly used to perform test on the users. Then the labeling result for each medical image can be obtained from the users. The labeling result for each medical image from the users is compared with correct labeling result, so as to obtain correct labeling rate for a medical images with correct labeling results. When the correct labeling rate is higher than the preset second threshold, it can be determined that the users have qualification to perform pathological labeling. Through screening labeling operators based on standard test, high medical level can be ensured, with consistent and stable labeling qualification, so as to ensure labeling qualification and obtain objective and scientific evaluation index and facilitate construction of machine learning model in the future.

In another preferable example, the method further comprises the following steps:

when the artificial labeling result for any one medical image from any one labeling user is consistent with the reference labeling result, increasing the correct labeling numbers of the said user by 1;

when the correct labeling numbers of the labeling user is higher than the preset threshold, incorporating this labeling user to the physician user library.

When the excellent labeling user who is incorporated into the physician user library obtain Certificate of Medical Practitioner, he/she can apply for physician user with qualification to issue report. As such, the problem about lack of physician users and overload working can be overcame, thereby relieving the pressure on issuing reports and enhancing efficiency of issuing reports.

As shown in FIG. 8, provided herein is a structural diagram illustrating a device for pathologically labeling the medical image according to one embodiment as described herein. The said device comprises:

an obtaining module 801 for pathological labeling qualification, for judging whether the user has pathological labeling qualification when receiving a request for entering into labeling mode inputted by any one user on the mobile terminal;

a displaying module 802 for medical images, for randomly calling medical images to be labeled and displaying such medical images at the displaying interface of the mobile terminal when judging that the user has qualification to perform pathological labeling;

a saving module 803 for the first labeling result, for receiving and saving the first labeling result for the medical images from the user.

The implementation and working principle of the device for pathologically labeling the medical image of the present example can refer to the above description on any methods for pathologically labeling for the medical images, without repeated description.

Another example provides a device for pathologically labeling the medical images, comprising: a processor, a memory and computer programs storing in the memory and configured to be executed by processor. When executing the computer programs by the processor, the method for pathologically labeling the medical images and the method for issuing a report according to any one of the above example can be achieved.

Another example of the present invention provides a computer-readable storage medium, comprising computer programs stored therein. When operating the computer programs, the method for pathologically labeling the medical images and the method for issuing a report according to any one of the above example can be executed on the device in which the computer-readable storage medium is contained.

Figure 9:
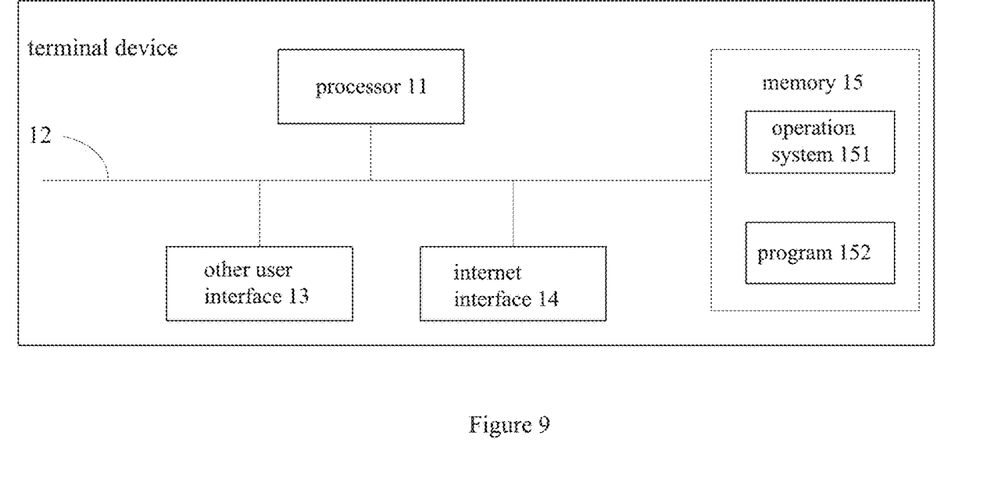
FIG. 9 is a structural diagram illustrating the terminal device according to one embodiment as described herein.

As shown in FIG. 9, it shows a structural diagram illustrating the terminal device according to one embodiment as described herein. The terminal device comprises at least one processor 11, such as CPU, at least one internet interface 14 or other user interface 13, a memory 15, and at least one communication bus 12, for achieving communication among these elements. The other user interface 13 to other users can alternatively comprise an USB port and other standard ports, wired port. The internet interface 14 can alternatively comprise a Wi-Fi port and other wireless ports. The memory 15 may comprise a high-speed RAM memory, or may alternatively comprise a non-volatile memory, for example, at least one disk memory. The memory 15 may alternatively comprise at least one storage device located remotely from the processor 11 as mentioned above.

In one embodiment, the following elements are stored in the memory 15:

an executable module or data structure or a subset thereof, or a superset thereof;

an operation system 151, comprising various system programs, such as batteries management system and the like, for achieving various basic operations and handling tasks based on hardware;

a program 152.

Particularly, the processor 11 is used to call the program 152 stored in the memory 15 to execute the method for pathologically labeling the medical images or the method for issuing a report about the medical images, such as step S1 as shown in FIG. 1. Or, when executing the computer program by the processor 11, the function of respective modules/units in the device according to the above example can be achieved, for example, the displaying module 802 for medical images.

Illustratively, the computer program can be divided into one or more modules/units which are stored in the memory and executed by the processor to achieve the present invention. The one or more modules/units may be a series instruction segments of computer program which can achieve specific function and can be used to describe the execution progress of the computer program in the terminal device.

The terminal device may include, but not limited to, a processor 11, a memory 15. It can be understood by the skilled in the art, the diagram is merely an illustration of the terminal device, without any limitation to the terminal device, which may comprise more or less elements than those shown in FIG. 9, or combine certain elements, or those different from those shown in FIG. 9. For example, the device for pathologically labeling the medical images may further comprise an inputting and outputting device, an internet access device, bus and the like.

The processor 11 may be a central processing unit (CPU), or other general-purpose processor, digital signal processor (DSP), an application specific integrated circuit (ASIC), a field-programmable gate array (FPGA), or other programmable logical devices, a discrete gate or transistor logical device, discrete hardware components and the like. The general-purpose processor may be micro-processors or any common processors and the like. The processor 11 is the controlling center of the terminal device, which can connect respective parts of the whole terminal device by using various ports and lines.

The memory 15 can be used to store the computer programs and/or modules. The processor runs or executes the computer programs and/or module stored in the memory, and calls the data stored in the memory to achieve various functions of the terminal device. The memory 15 may comprise an area for storage of programs and an area for storage of data. The area for storage of programs can store the operation system, at least one application program required for achieving functions (e.g., sound playing function, image playing function and the like). The area for storage of data may store data established according to use of cell phone (e.g., audio data, contacts and the like). In addition, the memory 15 may comprise a high speed random access memory, or a non-volatile memory such as a hard-disk, an internal memory, a plug-in hard disk, a smart media card (SMC), a secure digital (SD) card, a flash card, at least one disk storage device, a flash storage device, or other volatile solid storage device.

If the modules/units integrated with the terminal device are achieved in form of software function units and sold or used as an individual product, they can be stored in a computer-readable storage medium. Based on this, all of or part of process in the method as described in the above examples can be completed by relevant hardware depending on the instructions of the computer programs. The computer programs can be stored in a computer-readable storage medium and can be executed by the processor to achieve the steps in the methods as mentioned above. The computer programs comprise computer program codes which can be source codes, object codes, executable files or certain intermediate forms and the like. The computer-readable medium may comprise: any entities or devices, recording media, flash disks, mobile hard disks, disks, CDs, computer memories, read-only memories, random access memories, and software distribution media, which are capable of carrying the computer program codes. It should be noted that the content contained in the computer-readable medium can be increased or decreased as appropriate according to laws in other jurisdictions or patent practice.

The foregoing is provided for illustration, and does not intend to limit the present invention. Any changes and modifications for the above embodiments come within the scope of the present invention.

The invention claimed is:

1. A method for pathologically labeling medical images, which can be used in a mobile terminal, comprising the following steps:

judging whether a user has qualification to perform pathological labeling when receiving a request for entering into labeling mode inputted by any one user in the mobile terminal;

randomly calling medical images to be labeled and displaying them at thea displaying interface of the mobile terminal when judging whether the user has qualification to perform pathological labeling;

receiving and saving a first labeling result for the medical images from the user;

wherein:

the medical images are generated by the following steps:

dividing original scanning images of pathological section into n FOV images, and calculating a pathological index of each FOV image among n FOV images, wherein 10^10≥n≥10 and storage space occupied by the FOV images is less than a preset threshold;

obtaining first m FOV images with highest pathological index among n FOV images based on the pathological indexes of respective FOV images as the medical images, wherein 50≥m≥5;

the method further comprises the following steps:

judging whether first labeling results from two users are consistent with each other when detecting that any one medical image has two first labeling results from two users;

when judging that the two first labeling results from two users are consistent with each other, using the first labeling results from two users as a reference labeling result for the medical images and increasing correct labeling numbers for these two users by 1; and when judging that the first labeling results from two users are inconsistent with each other, randomly sending a request to label the medical images to any one other user or an expert user;

when receiving a second labeling result from any one other user or the expert user, using this second labeling result as a reference labeling result for the medical images, and increasing incorrect labeling numbers of the user whose first labeling result is inconsistent with the second labeling result by 1 and increasing the correct labeling numbers of the user whose first labeling result is consistent with the second labeling result by 1.

2. The method of claim 1, further comprising the following step:

when detecting that any one user's incorrect labeling numbers are higher than the preset first threshold, cancelling this user's qualification to perform pathological labeling.

3. The method of claim 1, further comprising the following steps:

when displaying the medical images, obtaining AI labeling results for the medical images, wherein the AI labeling results comprises positive and negative results;

when the AI labeling results are negative and the first labeling result for the medical images from any one user is consistent with the AI labeling results, using the AI labeling results as a reference labeling results for the medical images;

when the AI labeling results are positive and the first labeling results for the medical images from any two users are consistent with the AI labeling results, using the AI labeling results as reference labeling results for the medical images;

when the AI labeling results are positive and neither of the first labeling results for the medical images from any two users is consistent with the AI labeling results, using the first labeling results for the medical images from any two users as a reference labeling results for the medical images.

4. The method of claim 3, further comprising the following steps:

when the AI labeling results for the medical images are positive and the first labeling result for the medical images from one of any two users is inconsistent with the AI labeling results, randomly sending a request to perform labeling or organize discussion to any one of other users or expert users;

when receiving a second labeling result for the medical images from other users or expert users, using the second labeling result as a reference labeling result;

when receiving a third labeling result for the medical images made after discussion among any two users and other users or expert users, using the third labeling result as the reference labeling result.

5. The method of claim 1, wherein judging whether the user has qualification to perform pathological labeling comprises:

when receiving a request for qualification of labeling inputted by the user, displaying a test interface and randomly calling a medical images for performing test, and then obtaining a labeling result for each medical image from the user, wherein the a medical images for performing test have correct labeling results, and wherein a≥5;

comparing the labeling result for each medical image from the user with the correct labeling result and obtaining a correct labeling rate for the a medical images with correct labeling results;

determining that the user has qualification to perform labeling when the correct labeling rate is higher than a preset second threshold.

6. The method of claim 5, wherein judging whether the user has qualification to perform pathological labeling further comprises:

judging whether the correct labeling rate is higher than the preset third threshold when the correct labeling rate is lower than the preset second threshold;

when judging that the correct labeling rate is higher than the preset third threshold, displaying a training interface if the user sends a request to perform training, and then calling x medical images for training the user, wherein the x medical images have correct labeling results, and wherein x≥5.

7. The method of claim 6, wherein judging whether the user has qualification to perform pathological labeling further comprises:

when judging that the correct labeling rate is lower than the third threshold, displaying a learning interface on which systematic knowledges about labeling are indicated.

8. The method of claim 7, wherein judging whether the user has qualification to perform pathological labeling further comprises:

when judging that the correct labeling rate is lower than the third threshold, refusing the user's request to perform training and labeling within a preset period;

when judging that the correct labeling rate is lower than the third threshold, receiving the user's request to perform training and labeling again after the preset period.

9. The method of claim 1, wherein receiving and saving the first labeling result for the medical images from the user comprises:

displaying first option buttons indicating whether there are lesion cells and what type of the lesion cells at the displaying interface at the time of displaying the medical images;

when receiving a clicking operation on the first option buttons from the user, obtaining and saving the first labeling results for the medical images from the user.

10. The method of claim 9, wherein obtaining the first labeling results for the medical images from the user when receiving the clicking operation on the first option buttons from the user comprises the following steps:

displaying labeling results for the medical images from other users or machines at the displaying interface at the time of displaying the medical images and meanwhile, displaying second option buttons indicating whether agreeing with the labeling results for the medical images from other users or machines;

obtaining the first labeling results for the medical images from the user when receiving the clicking operation on the second option buttons from the user.

11. The method of claim 1, further comprising the following step:

when receiving a request to incorporate the medical images into difficult case library from other users or expert users, incorporating the medical images into the difficult case library.

12. The method of claim 10, wherein the second option buttons comprises an agreement button and a disagreement button; and wherein obtaining the first labeling results for the medical images from the user when receiving the clicking operation on the first option buttons from the user comprises the following steps:

when receiving the clicking operation on the agreement button from the user, using the labeling results for the medical images from other users or machines as the first labeling results from the user;

when receiving the clicking operation on the disagreement button from the user, using the labeling results inputted by the user as the first labeling results.

13. The method of claim 12, further comprising the following steps:

displaying a voice inputting mark at the time of displaying the second option buttons, wherein the displaying status of the voice inputting mark includes detection of voice inputting and termination of detection of voice inputting;

wherein when receiving the clicking operation on the disagreement button from the user, using the labeling results inputted by the user as the first labeling results comprises the following step:

when receiving the clicking operation on the disagreement button from the user, changing the displaying status of the voice inputting mark to detection of voice inputting and obtaining the labeling results inputted by the user via a voice obtaining device as the first labeling results.

14. The method of claim 13, wherein the voice inputting mark is a progress bar of voice inputting, when the displaying status of the voice inputting mark is termination of detection of voice inputting, a full grid of the progress bar of voice inputting is displayed at the displaying interface; when the displaying status of the voice inputting mark is detection of voice inputting, the progress bar of voice inputting is displayed as gradually decreasing progress bar within a preset period.

15. A device for pathologically labeling medical images, comprising a processor, a memory and computer programs stored in the memory and configured to be executed by the processor, wherein, the method for pathologically labeling medical images of claim 1 is achieved when the computer programs are executed by the processor.

16. A computer-readable storage medium, comprising stored computer programs, wherein the device in which the computer-readable storage medium exists is controlled to execute the method for pathologically labeling medical images of claim 1 when operating the computer programs.

* * * * *